United States Patent
Kurosawa

(10) Patent No.: US 8,751,267 B2
(45) Date of Patent: Jun. 10, 2014

(54) MEDICAL IMAGE PROCESSING SERVER AND MANAGING METHOD FOR MEDICAL IMAGE PROCESSING SERVER

(75) Inventor: Hiroshi Kurosawa, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 183 days.

(21) Appl. No.: 13/166,015

(22) Filed: Jun. 22, 2011

(65) Prior Publication Data

US 2011/0320218 A1    Dec. 29, 2011

(30) Foreign Application Priority Data

Jun. 24, 2010    (JP) .................. 2010-144079

(51) Int. Cl.
*G06Q 50/00*    (2012.01)
*G06Q 50/24*    (2012.01)

(52) U.S. Cl.
CPC ..................... *G06Q 50/24* (2013.01)
USPC ............... 705/3; 382/128; 382/131

(58) Field of Classification Search
CPC ..... G06F 19/321; G06F 19/322; G06Q 50/24; G06Q 50/22; A61B 5/0013
See application file for complete search history.

(56) References Cited

U.S. PATENT DOCUMENTS 6,551,243 B2 *  4/2003  Bocionek et al. ............. 600/300
8,253,806 B2 *  8/2012  Mikawa et al. ............ 348/207.1

FOREIGN PATENT DOCUMENTS

| JP | 2006-113958 | 4/2006 |
| JP | 2009-087230 | 4/2009 |
| JP | 2010-104614 | 5/2010 |

OTHER PUBLICATIONS

Office Action dated Feb. 25, 2014, in Japanese Patent Application No. 2010-144079, filed Jun. 24, 2010 (2 pages).
Notes/Domino Magazine, May 5, 2001, vol. 6, No. 5, pp. 70-73 (w/ English-language Translation), 8 pages.
WindowsMode, Jul. 24, 2007, vol. 12, No. 9, pp. 106-109 (w/English-language Translation), 7 pages.

* cited by examiner

*Primary Examiner* — Michelle L Le
(74) *Attorney, Agent, or Firm* — Oblon, Spivak, McClelland, Maier & Neustadt, L.L.P.

(57) ABSTRACT

A medical image processing server, connected with terminals, has an access time obtaining unit, an update time obtaining unit, a determining unit and a data outputting unit. The access time obtaining unit obtains an access start time at which each of the terminals accesses medical image data selected by each of the terminals. The update time obtaining, if each of the terminals issues an update request for edited medical image data, obtains a last update time of the edited medical image data. The determining unit determines whether to generate updated data or copied data of medical image data edited by one of the terminals based on the access start time obtained by the terminal and the last update time obtained by another of the terminals. The data outputting unit outputs the updated data and the copied data based on identification information complying with a predetermined medical protocol.

10 Claims, 15 Drawing Sheets

Report

2010/05/19 163855.ID  20100519 163855.Name  
Hospital Name  Adult Heart  
2010/05/19 4:44:35 PM

Measure

Cardiac_2 ▽  The report shows averaged value. Check all data.

LV MOD Simpson

| ESV | 3.2 | ml |
| LVLs Diff | -37.0 | % |
| LVAd2 | 0.67 | cm2 |
| LVLd2 | 10.9 | mm |
| EDV2 | 0.4 | ml |
| LVAs2 | 3.66 | cm2 |
| LVLs2 | 23.0 | mm |
| ESV2 | 5.3 | ml |
| SV2 | -4.9 | ml |
| EF2 | -1225.0 | % |

| LVAs2 | 3.66 | cm2 |
| LVLs2 | 23.0 | mm |
| ESV2 | 5.3 | ml |

Comment

2010/01/20  CCCCC  
O:o:sajsadlkjlkjhd::sim,/e  
Pwpofaihggprolmmbsass  
klndfn:kvseuibjlwhgai  
Al,l:wp:jo/vroi:awok30mg  
mh7

2010/1/25  AAAAA  
Webbbkeoialrgih  
Sadoaiulihk:  
weljie:lpsflosahlo

Send as DICOM | Work Sheet | Print All | Crear All

11

☐ All List ○ Mark △▽

| | Data | Type |
| ○ | Current | Pediatric Heart |

FIG. 15

MEDICAL IMAGE PROCESSING SERVER AND MANAGING METHOD FOR MEDICAL IMAGE PROCESSING SERVER

CROSS-REFERENCE TO RELATED APPLICATION

This application is based upon and claims the benefit of priority from Japanese Patent Application No. 2010-144079, filed on Jun. 24, 2010, the entire contents of which are incorporated herein by reference.

FIELD

Embodiments of the present invention relate to a medical image processing server and a managing method for the medical image processing server that manages a medical information system.

BACKGROUND

In recent years, thin-client-based information processing systems have received attention and medical service has started introducing the thin-client-based systems. The thin-client-based medical system has a network such as a hospital LAN through which a single server and multiple clients (thin client terminals) are connected with each other. In the network, the thin client terminals do not contain hard disk drives and the server stores therein data and an application to cause the thin client terminals to operate. Specifically, the server stores therein data of an image took by another image processing equipment, performs image processing, and activates various application programs in response to requests from the thin client terminals. The thin client terminals have only a data displaying function and a minimum inputting function.

The thin client terminals do not store therein application programs and data, so that processing loads of the thin client terminals can be reduced and data can be centrally managed on the server. In addition, since the thin client terminals do not contain hard disk drives, the thin client terminals are inexpensive and an increased number of thin client terminals can be introduced and connected with the network.

In the thin-client-based systems, a plurality of users may access same data on the server through their own thin client terminals. Also, while a plurality of thin client terminals are concurrently accessing same data on the server, the thin client terminals may update the data. Conventionally, in such a case where a user is accessing data on the server, another user can read but cannot update the data. In addition, assume that when a plurality of users are concurrently accessing same data, one of the users tries to update this data. If another user has already updated the data, it is determined which of the modifications will be made to the original data.

However, at health care sites, for example in emergency situations, if a user cannot update data because another user is accessing the data, the data cannot be updated to latest data. Also in a situation that occurs when a plurality of users are concurrently accessing same data, where one of modifications to the data is needed to be selected, an operating mistake may delete the data, resulting in a re-examination or a misdiagnosis.

BRIEF DESCRIPTION OF THE DRAWINGS

In accompanying drawings,

FIG. 15 is a diagram showing an exemplary display of a report and details of the report.

DETAILED DESCRIPTION

Hereinafter, a medical image processing server and a managing method for the medical image processing server according to the embodiments will be described with reference to the accompanying drawings.

To solve the above-described problems, the medical image processing server, connected with a plurality of terminals via a network, according to the present embodiment has: a storing unit configured to store medical image data; an access time obtaining unit configured to obtain an access start time at which each of the terminals accesses medical image data selected by each of the terminals; an update time obtaining unit configured to, if each of the terminals edits the medical image data and issues an update request for the edited medical image data, obtain a last update time of the edited medical image data; a determining unit configured to, if one of the terminals issues the update request, determine whether to generate updated data or copied data of medical image data edited by the terminal based on the access start time obtained by the terminal and the last update time obtained by another of the terminals; and a data outputting unit configured to output the updated data and the copied data as data derived from the medical image data based on identification information complying with a predetermined medical protocol.

To solve the above-described problems, the managing method for the medical image processing server, connected with a plurality of terminals via a network, according to the present embodiment has: obtaining an access start time at which each of the terminals accesses medical image data selected by each of the terminals; obtaining, if each of the terminals edits the medical image data and issues an update request for the edited medical image data, a last update time of the edited medical image data; determining, if one of the terminals issues the update request, whether to generate updated data or copied data of medical image data edited by the terminal based on the access start time obtained by the terminal and the last update time obtained by another of the terminals; and outputting the updated data and the copied data as data derived from the medical image data based on identification information complying with a predetermined medical protocol.

Figure 1:
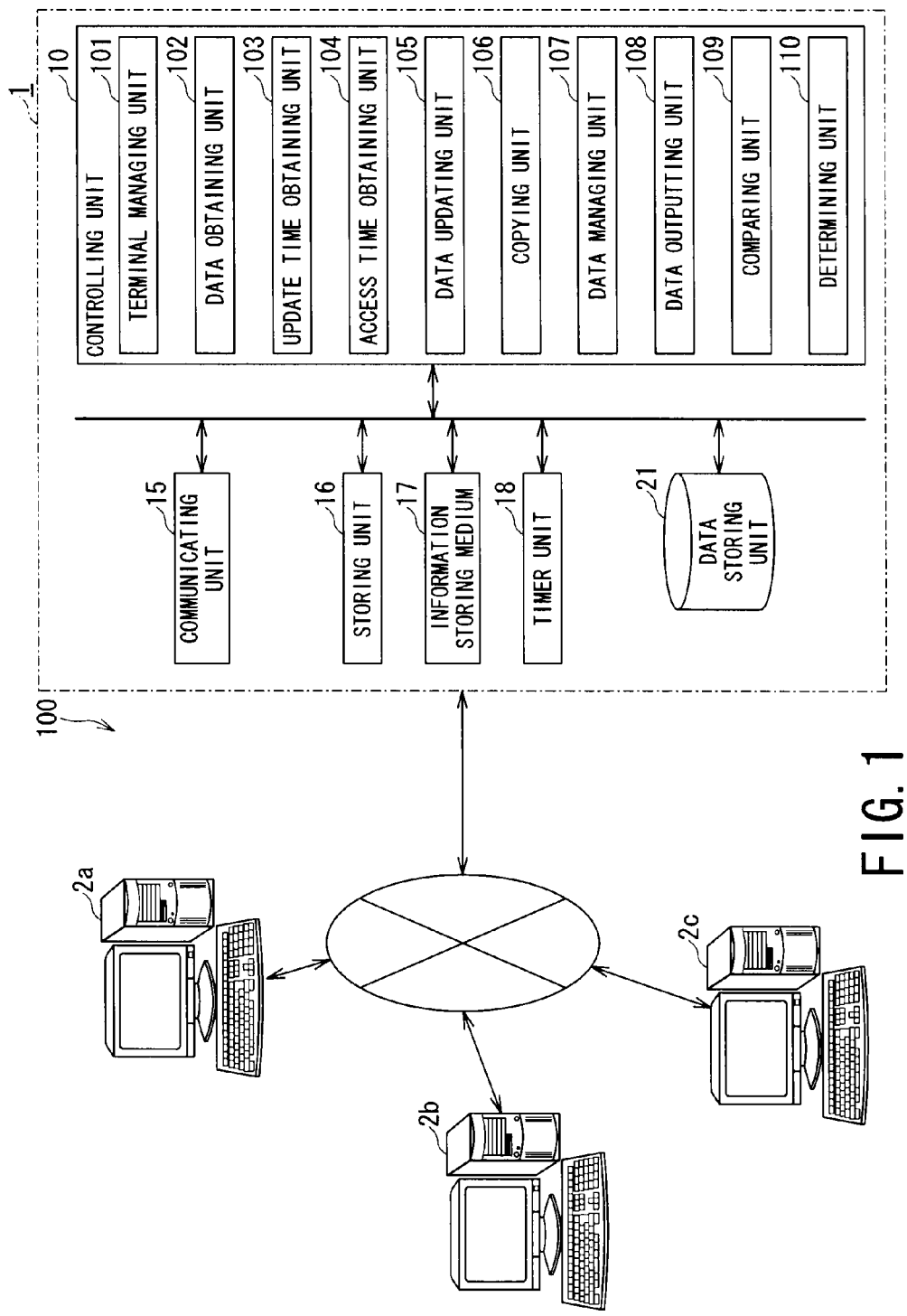
FIG. 1 is a configuration diagram showing a server according to an embodiment, and showing a network system for connecting the server with thin client terminals.

FIG. 1 a configuration diagram showing a server 1 (medical image processing server) according to an embodiment of the present invention, and showing a network system for connecting the server 1 with thin client terminals 2 (2a, 2b, 2c, and so on). The server 1 is a unit of the thin-client-based medical information system 100. The server 1 is connected and communicated with the thin client terminals 2 via a LAN (local area network) in a hospital.

The thin client terminals 2 are viewed and operated by users and each include a displaying unit and an operating unit. The displaying unit displays data stored in the server 1. The operating unit receives various inputs and makes a command to store data in the server 1. Since the embodiment is the thin-client-based network system, the server 1 has applications to operate the thin client terminals 2, and such an application and a hard disk drive to store therein data are not installed in the thin client terminals 2. The thin client terminal 2 is connected to the server 1 to perform various types of processing such as viewing and editing the data stored in the server 1. Also, the thin client terminals 2a, 2b, 2c, and so on can concurrently access the same data on the server 1.

The server 1 includes a controlling unit 10, a communicating unit 15, a storing unit 16, an information storing medium 17, a timer unit 18, and a data storing unit 21, which are connected and communicated with each other via a bus.

The communicating unit 15 is connected with the LAN in the hospital to communicate with the thin client terminals 2. The timer unit 18 clocks times at which the thin client terminals 2 start to access data as well as a time at which data is updated.

The data storing unit 21 stores therein data of a patient image took by a diagnostic imaging equipment, not shown, and examination data including text data such as a report on an examination. The image data and the text data in the examination data have accompanying data attribute information such as a name of an equipment that generates the data, data sizes, a name of a terminal that performs editing, a last updated time, and the like.

The storing unit 16 functions as a working area for the controlling unit 10 and the communicating unit 15, and may be RAM (Random Access Memory) or the like. The storing unit 16 also temporarily stores the time clocked by the timer unit 18.

The information storing medium 17 (medium readable by computers) stores therein a program and data, and may be a hard disk drive or memory (Flash Memory and ROM (Read Only Memory)). The information storing medium 17 stores therein a program to cause a computer to function as each unit of the embodiment (a program to cause a computer to execute processing of each unit), a plurality of applications to cause the thin client terminals 2 (2a, 2b, 2c, and so on) to operate, and the like.

The controlling unit 10 is a calculating device that controls the entire server 1 and executes processing according to a basic program such as an OS (Operating System) and a predetermined program stored in the information storing medium 17.

The controlling unit 10 includes a terminal managing unit 101, a data obtaining unit 102, an update time obtaining unit 103, an access time obtaining unit 104, a data updating unit 105, a copying unit 106, a data managing unit 107, a data outputting unit 108, a comparing unit 109, and a determining unit 110.

The terminal managing unit 101 authenticates the thin client terminals 2a, 2b, 2c, and so on, which are connected with the server 1, and manages the connected terminals. The data obtaining unit 102 obtains examination data in the data storing unit 21 based on an access request from the thin client terminals 2. The examination data has a predetermined examination ID (Identification), and includes an examination name, information of a patient who has undergone an examination, examination contents, an examination date, data update date, data of at least one image took in the examination, an examination report, and the like.

The update time obtaining unit 103 obtains a time at which the examination data is last updated. The access time obtaining unit 104 obtains the time clocked by the timer unit 18 at which the thin client terminal 2 starts to access the examination data.

The comparing unit 109 compares the last update time of the examination data, the time being obtained by the update time obtaining unit 103, with the start time of access to the examination data, the time being obtained by the access time obtaining unit 104. Details will be described below.

The determining unit 110 determines whether to update the original data by overwriting the original data with the data edited by the thin client terminal 2 or to generate a copy of the edited data on the basis of the last update time of the examination data and the start time of the access to the examination data, which are compared by the comparing unit 109.

The data updating unit 105 updates the original data by overwriting this original data with the data edited by the thin client terminal 2. The copying unit 106 generates the data edited by the thin client terminal 2 as copied data of the original data.

The data managing unit 107 collectively manages the data updated from the original data by the data updating unit 105 and the copied data items generated by the copying unit 106 as data derived from the original data. The data outputting unit 108 outputs the copied data items generated by the copying unit 106 to an external device. Details will be described below.

<Exemplary Server Operation>

Figure 2:
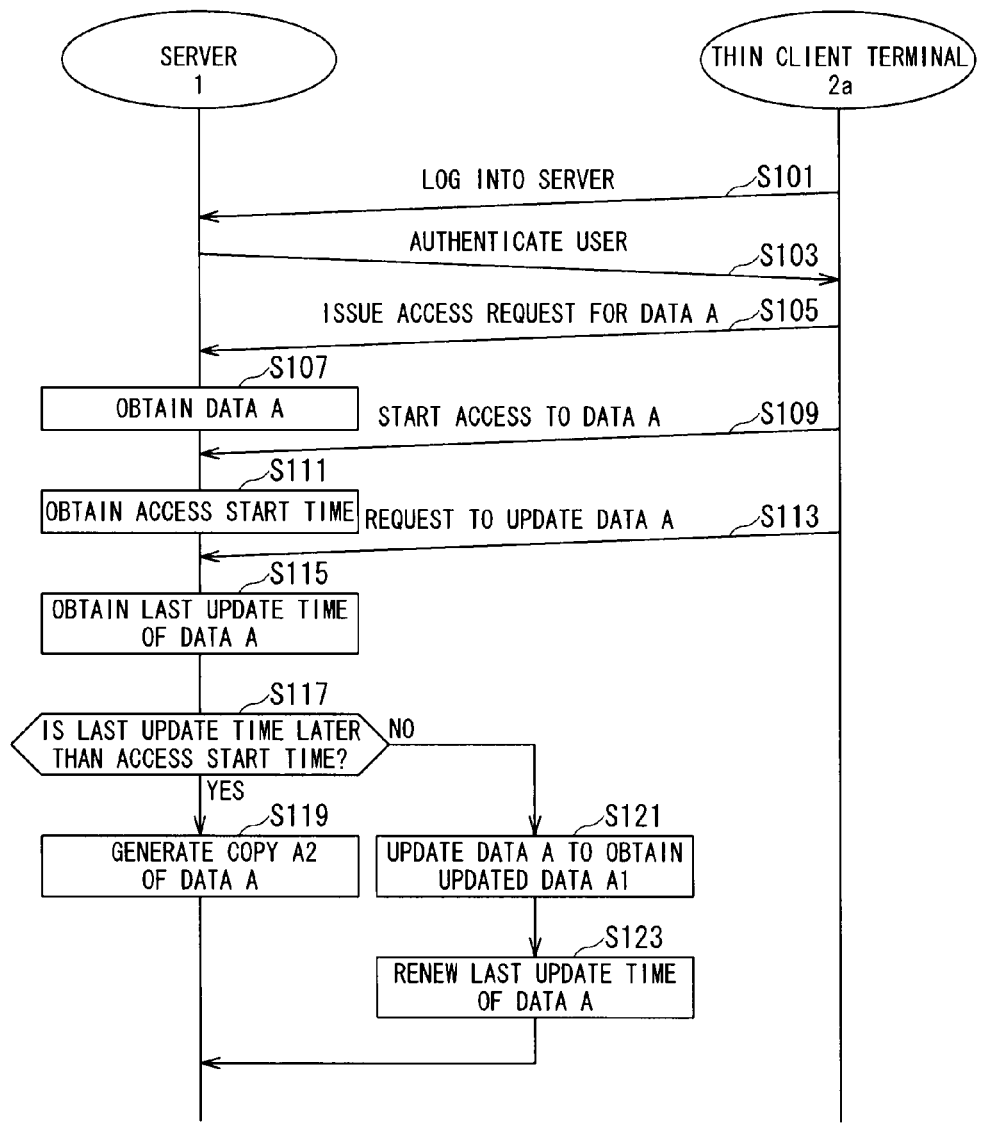
FIG. 2 is a flow chart showing an exemplary operation between the server and the thin client terminals in a medical information system.

Next, an exemplary operation between the server 1 having the above-described configuration and the thin client terminal 2a will be described with reference to a flow chart of FIG. 2. In this embodiment, assume that data is examination data A.

When a user logs in thorough the thin client terminal 2a to access the server 1 (step S101), the terminal managing unit 101 of the server 1 authenticates the thin client terminal 2a (step S103). The user then issues an access request for the examination data A stored in the data storing unit 21 by using the thin client terminal 2a authenticated in step S103 (step S105). The data obtaining unit 102 of the server 1 obtains the examination data A from the data storing unit 21 in response to the access request issued in step S105 (step S107).

When the thin client terminal 2a then starts to access the examination data A obtained by the data obtaining unit 102 in step S107 (step S109), the timer unit 18 clocks a time at which the access to the examination data A is started, and the access time obtaining unit 104 obtains the access start time (step S111).

When the thin client terminal 2a then edits data included in the examination data A and requests to update the examination data A so as to save the edited data (step S113), before actually updating the examination data A, the update time obtaining unit 103 obtains a last update time of the examination data A based on a data update date included in the examination data A (step S115).

The comparing unit 109 then compares the start time of access to the examination data A, the time being obtained by the access time obtaining unit 104 in step S111, with the last update time of the examination data A, the time being obtained by the update time obtaining unit 103 in step S115. The determining unit 110 then determines, based on a comparison result obtained by the comparing unit 109, whether or not to generate a copy. If the last update time is later than the access start time (in step S117, "Yes"), the thin client terminal 2a and another thin client terminal (assume that this client terminal is a thin client terminal 2b) are concurrently accessing the examination data A, and the thin client terminal 2b has updated the examination data A before the thin client terminal 2a. Therefore, at this point, if the thin client terminal 2a updates the original examination data A with the data edited from this examination data A, the data updated by the thin client terminal 2b will be deleted. Therefore, the determining unit 110 determines to generate copied data, and the copying unit 106 generates a copy of the data edited by the thin client terminal 2a as copied data A2 and stores the data A2 in the data storing unit 21 (step S119).

If the last update time is earlier than the access start time (in step S117, "No"), another thin client terminal has not updated the examination data A since the access by the thin client terminal 2a. Therefore, the determining unit 110 determines to update the data without generating copied data. The data updating unit 105 updates the examination data A to generate updated data A1 in response to an update request from the thin client terminal 2a, and stores the updated data A1 in the data storing unit 21 (step S121). At this time, the timer unit 18 clocks a time at which the data is updated in step S121, and the data updating unit 105 renews the last update time obtained by the update time obtaining unit 103 in step S115 with the clocked time (step S123).

Figure 3A:
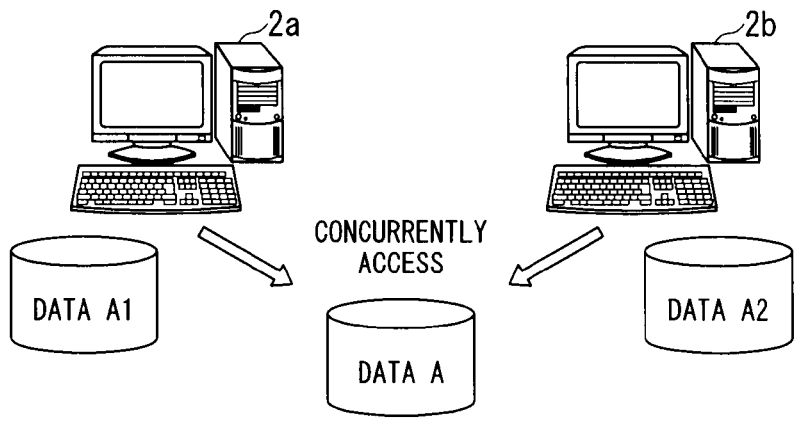
FIGS. 3A to 3C are conceptual diagrams showing access to the sever from two thin client terminals.
Figure 3B:
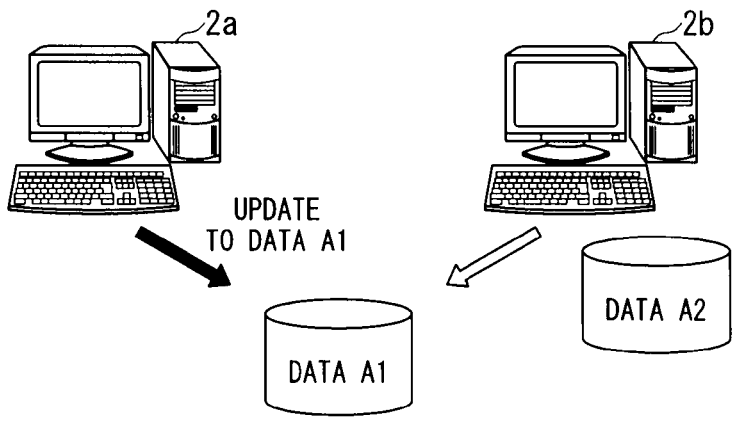
Figure 3C:
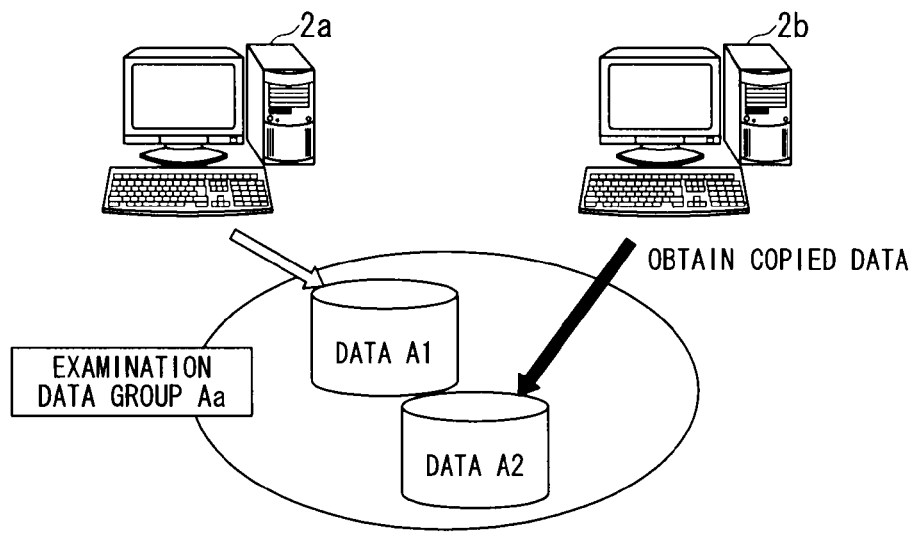

FIGS. 3A to 3C are conceptual diagrams showing access to the server from the thin client terminal 2a and the thin client terminal 2b. It is assumed that the thin client terminal 2a and the thin client terminal 2b are concurrently accessing the examination data A (FIG. 3A), data edited by the thin client terminal 2a is data A1 and data edited by the thin client terminal 2b is data A2. If the thin client terminal 2a updates the data A with the edited data A1 earlier than the thin client terminal 2b, the updated data A1 is stored in the server 1 (FIG. 3B). Thereafter, if the thin client terminal 2b tries to update the examination data A in the server 1 with the data A2, since the examination data A itself has already been updated with the updated data A1, the server 1 separately generates the data A2 as copied data (FIG. 3C). The updated data A1 and the copied data A2 are collectively managed in an examination data group Aa by the data managing unit 107 as data derived from the same examination data A.

<Exemplary List Screen>

Figure 4:
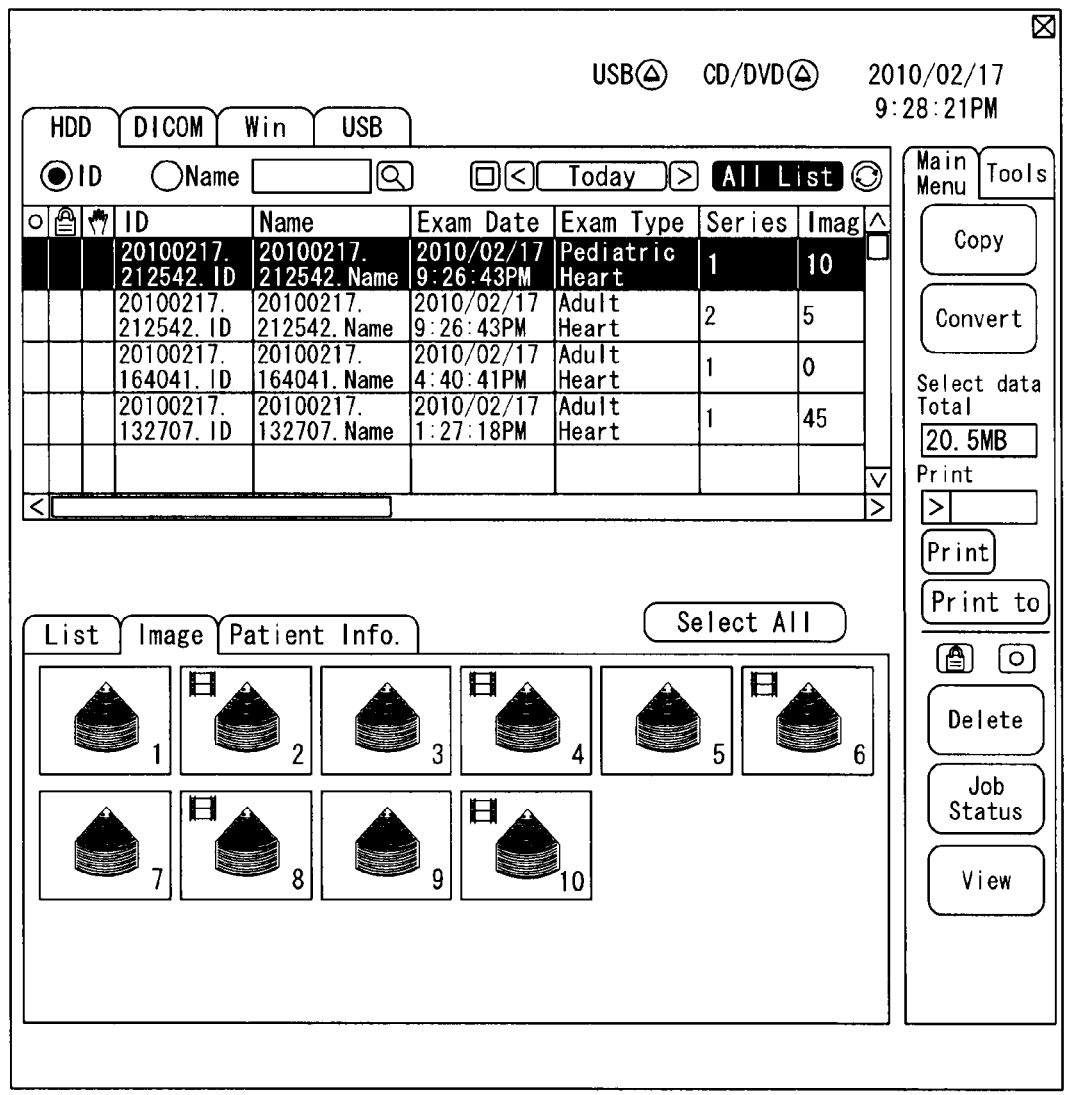
FIG. 4 is a diagram showing an exemplary screen of a list of data if the thin client terminal accesses the server.

FIG. 4 is a diagram showing an exemplary screen of a list of all examination data items in the server 1, the list being displayed on a thin client terminal 2 if the thin client terminal 2 accesses the server 1. An upper part of the screen shows a list of an examination ID (ID), a patient ID (Name), an examination date (Exam Date), an examination type (Exam Type), the number of took image data (Image), and the like of each examination data item stored in the server 1. A lower part of the screen shows thumbnails of image data, moving image data, and text data included in examination data selected from the list shown in the upper part of the screen. In FIG. 4, the examination data A of an examination ID "20100217.212542.ID" is being selected from the list, and in the lower part of the screen, ten thumbnails of CT image data or moving image data associated with the examination data A are displayed. As the moving image data, a thumbnail of a starting picture of the moving images is displayed.

Figure 5A:
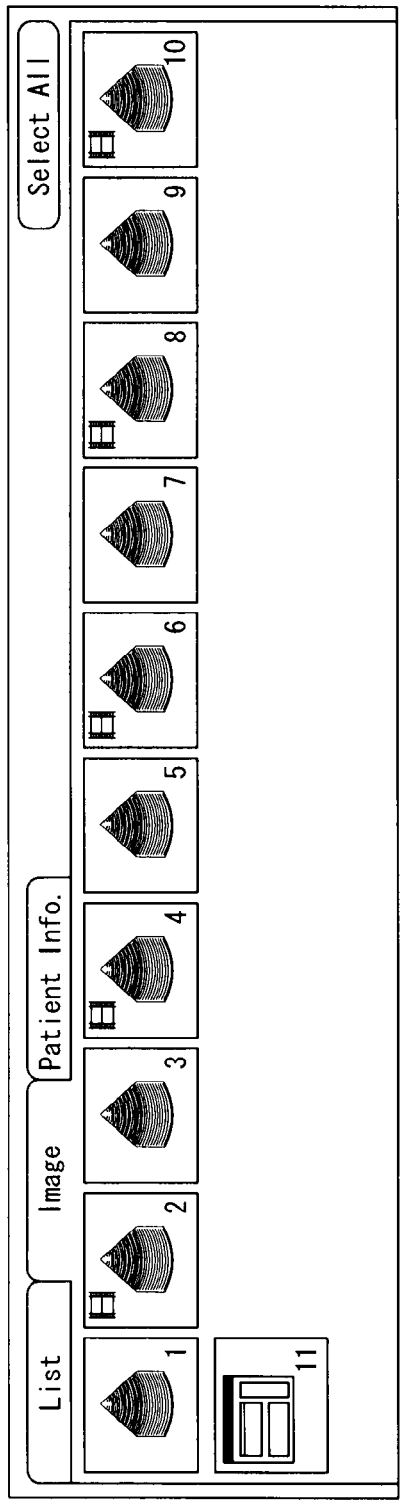
FIG. 5A is a diagram showing a screen example of thumbnails displayed on one thin client terminal.
Figure 5B:
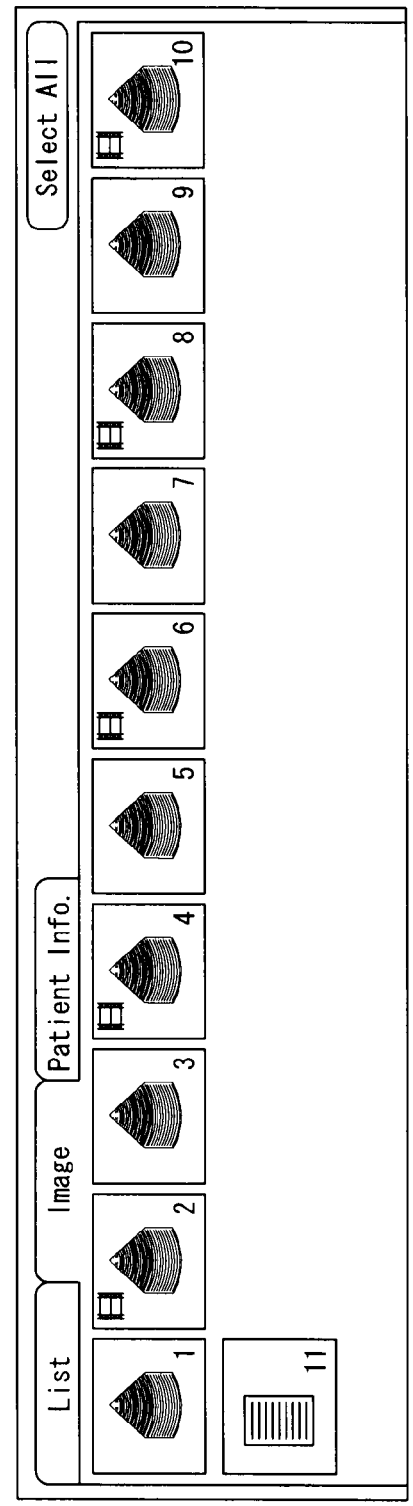
FIG. 5B is a diagram showing a screen example of thumbnails displayed on the other thin client terminal.

When the thin client terminals 2a and 2b are concurrently accessing the examination data A and the examination data A is edited by each of the terminals 2a and 2b, a screen example of thumbnails displayed on the thin client terminal 2a is shown in FIG. 5A, and a screen example of thumbnails displayed on the thin client terminal 2b is shown in FIG. 5B. The thin client terminal 2a adds a screen shot of the entire screen as an 11th data item. The thin client terminal 2b adds an examination report (text data) as an 11th data item. In this manner, since the thin client terminals 2a and 2b are concurrently accessing the examination data A, both the thin client terminals edit original ten images included in the original examination data A, so that each of the thin client terminals does not understand the updates by the opposite terminal. Therefore, an update by one thin client terminal is not reflected in data editing by the other thin client terminal.

Figure 6:
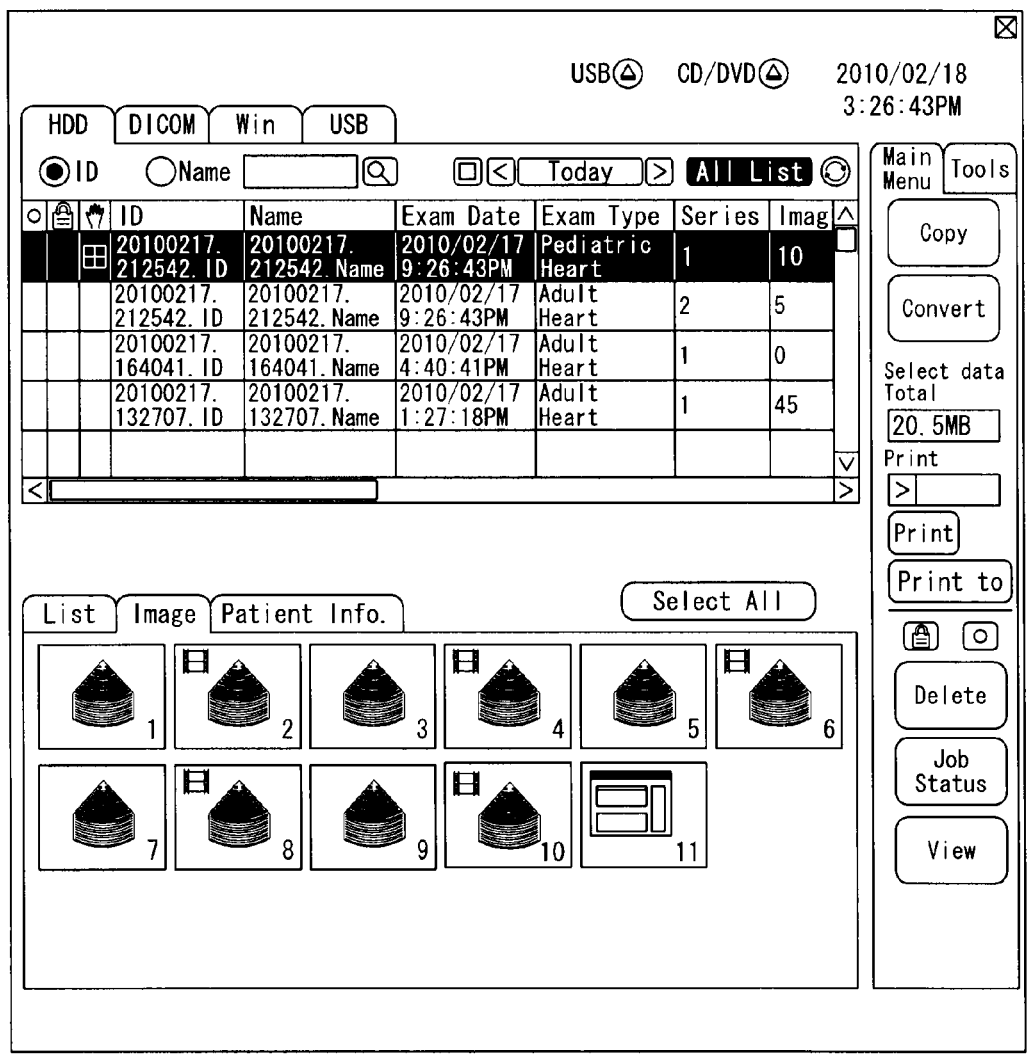
FIG. 6 is a diagram showing an exemplary screen of list that is displayed on the thin client terminal if copied data is generated.
Figure 7:
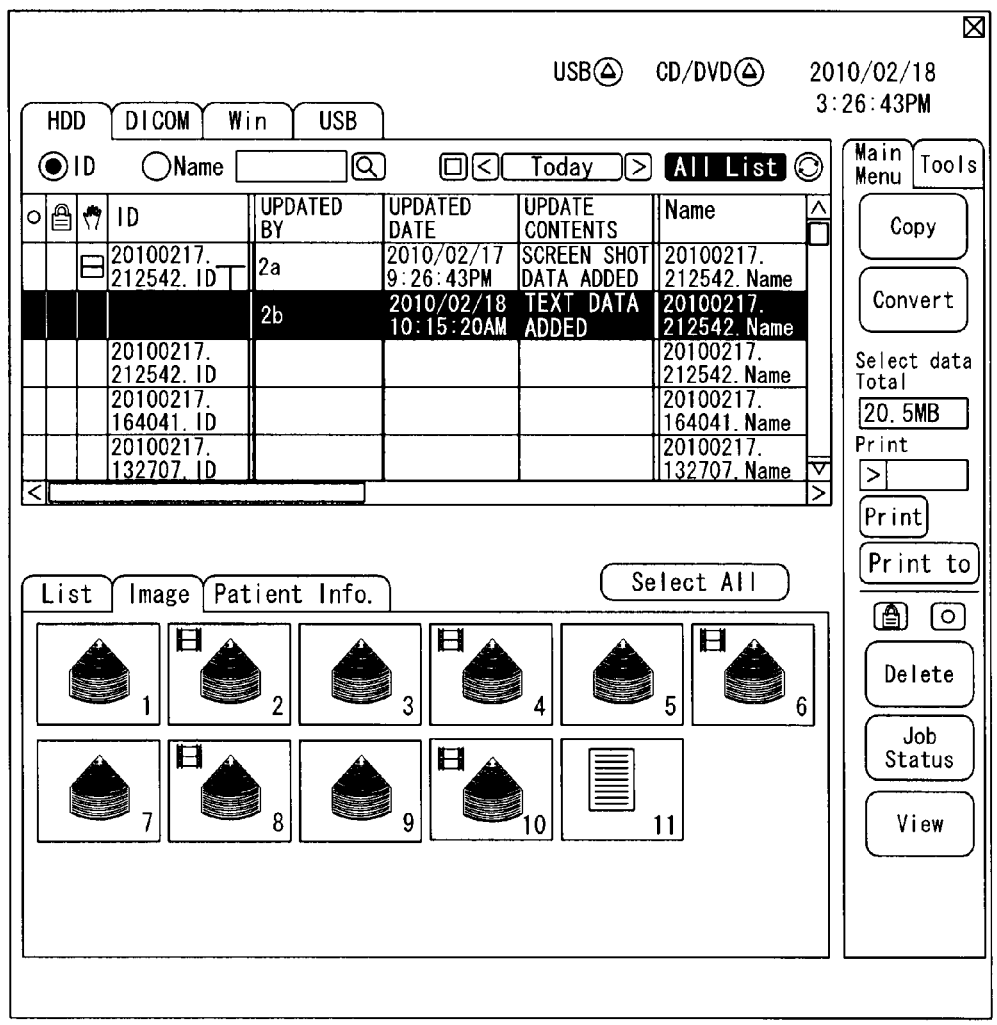
FIG. 7 a diagram showing an exemplary screen of list that is displayed on the thin client terminal if an item is expanded.

FIGS. 6 and 7 a diagram showing exemplary screens of lists that are displayed on the thin client terminal 2a if copied data is generated. FIG. 6 shows a list of all the examination data items displayed when the thin client terminal 2a accesses the server 1, and a + sign is appended to the beginning of an examination data item in which a copy has been generated. If the + sign is selected, as shown in FIG. 7, the item is expanded and details of all the copied data items in the data group are displayed. At this time, the list additionally shows columns of a person who has updated the data, an update date, and update contents. Thus, all the copied data items in the data group including data generated by another thin client terminal can be viewed through the thin client terminal 2a. For example, as shown in FIG. 7, in the expanded examination data A (assume that the data A is data of the examination ID "20100217.212542.ID"), if the examination data updated by the person on the thin client terminal 2b is selected, the copied data generated by the thin client terminal 2b, namely, the 11 thumbnails of the data items, in which the text data is added, as shown in FIG. 5B described above, are displayed in the lower part of the screen.

<Data Output>

Next, an exemplary operation to output all the updated data and copied data included in any examination data group stored in the data storing unit 21 of the server 1 to an external storing device and medical equipment will be described with reference to FIG. 8. The thin client terminal 2a, the thin client terminal 2b, and the thin client terminal 2c are concurrently accessing the examination data A. It is assumed that the data storing unit 21 of the server 1 stores, as the examination data group Aa, the updated data A1 edited by the thin client terminal 2a, with which the examination data A is updated, the copied data A2 edited by the thin client terminal 2b, and the copied data A3 edited by the thin client terminal 2c.

The data outputting unit 108 of the server 1 that receives from the thin client terminal 2a a request to output the examination data group Aa outputs, from the data stored in the data storing unit 21, data included in the examination data group Aa based on a predetermined condition. It should be noted that the output complies with a standard of the medical equipment, the DICOM (Digital Imaging Communications and Medicine) format. Examples of the predetermined condition involving the output include the three ways shown in FIG. 8.

Figure 8:
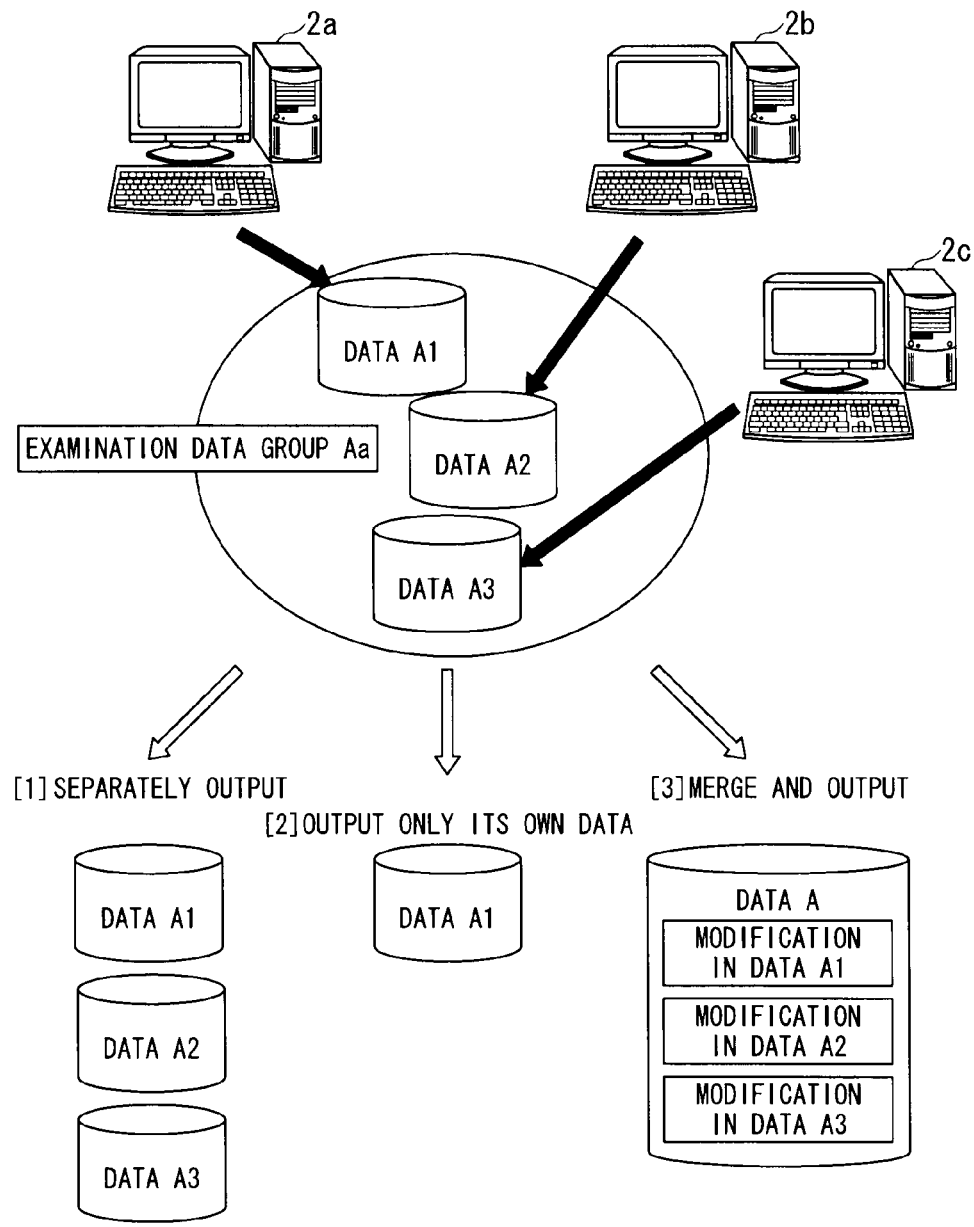
FIG. 8 is a conceptual diagram if update data and the copied data are output to an external storing device and medical equipment.

In a first example shown in [1] of FIG. 8, the data outputting unit 108 of the server 1 separately outputs all the data items A1, A2, and A3 included in the examination data group Aa. However, in the DICOM format typically, the data structure of the examination data group Aa, namely, the data structure in which a plurality of copied data items are generated from a single data item cannot be treated as it is. Therefore, when the data is output to external medical equipment as it is and the output data is returned to the server 1, the data items A1, A2, and A3 are separate data items that are not linked with each other.

Therefore, when each of the data items A1, A2, and A3 is output, a "Private Data" command for the DICOM format is used. With the "Private Data" command, any information about data can be written. When the data is output, information that each of the image data items A1, A2, and A3 is derived from the examination data A (that is, information that the image data items A1, A2, and A3 are included in the examination data group Aa) is added to "Private Data" of each of the data items A1, A2, and A3. Thereby, when the data output to the external medical equipment is returned and stored into the server 1, because each of the data items A1, A2, and A3 holds by "Private Data" the information that the data items are included in the examination data group Aa, each of the data items A1, A2, and A3 can be restored to the original data structure. As a result, the server 1 can display the data list on the thin client terminals 2 based on the data items A1, A2, and A3 returned to the server 1 and the added information.

In a second example shown in [2] of FIG. 8, the server 1 outputs only the data edited by the thin client terminal that issues an output request. For example, if the thin client terminal 2a issues an output request to the server 1, the server 1 outputs only the data A1.

In a third example shown in [3] of FIG. 8, the server 1 merges and then outputs the data items A1, A2, and A3 in the examination data group Aa. That is, modifications in the data items A1, A2, and A3, for the original examination data A are merged into one data set, the modification data set is made to the original examination data A, and then the resultant examination data is output.

For example, in FIG. 5A and FIG. 5B mentioned above, if the data in the thin client terminal 2a and the data in the thin client terminal 2b are merged and output, 12 pictures, namely, ten pictures of CT image data or moving image data as well as a screen shot added by the thin client terminal 2a and an examination report (text data) added by the thin client terminal 2b are output.

It should be noted that a condition to output the data in FIG. 8 may be changed according to an output destination. For example, if the data is output to a medium such as a CD-ROM, only the data edited by the thin client terminal that has issued the output request may be output because of a limited data amount. If the data is output to another server, all the data items may be separately output.

<Image Data Update>

Although the generation of the updated data and the copied data of the entire examination data has been described, updated data and copied data of individual image data items included in the examination data can be generated in the same manner. An exemplary case in which a plurality of thin client terminals are concurrently accessing any image data items included in the examination data will be described below.

Figure 9:
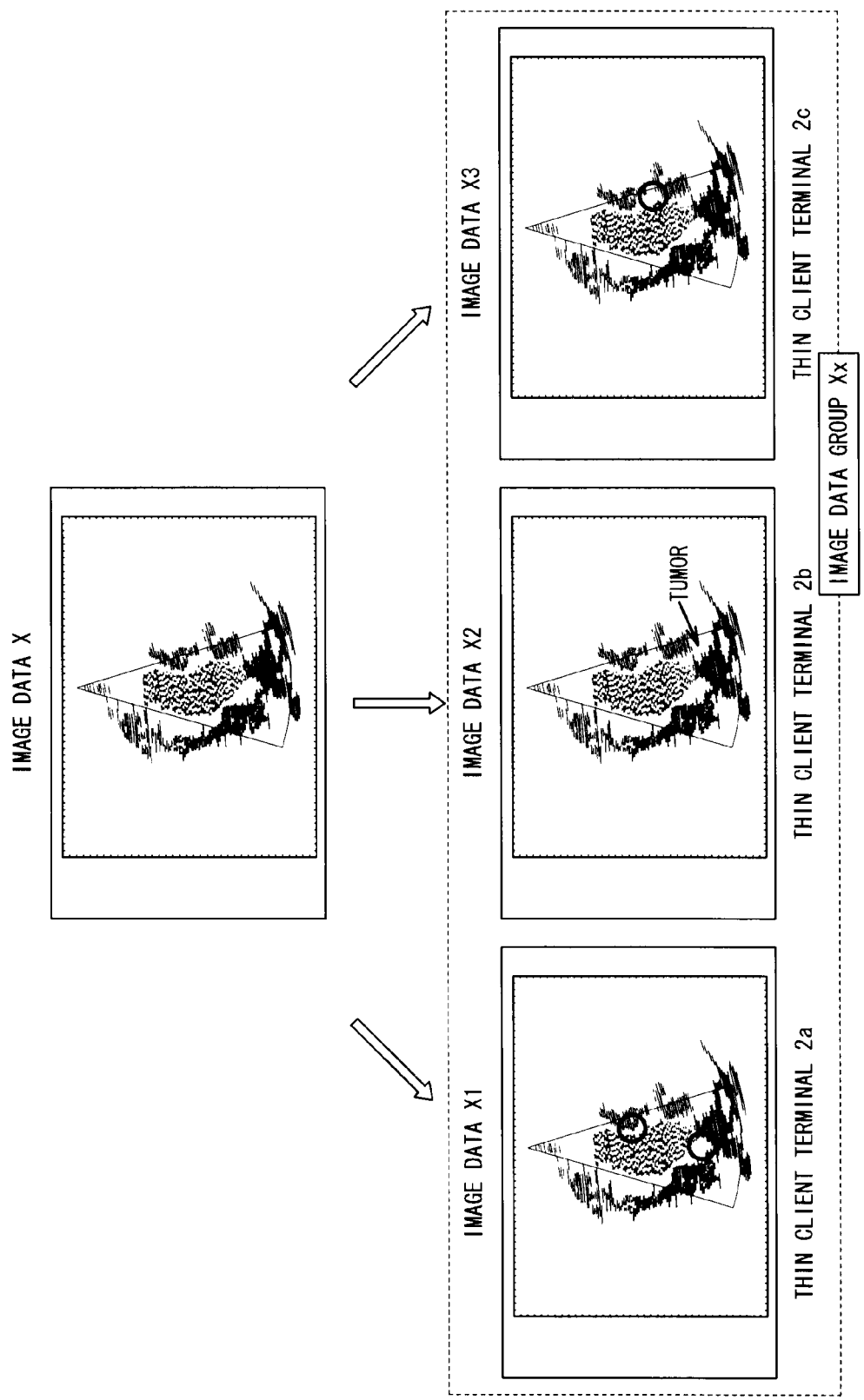
FIG. 9 is a diagram showing original image data and image data items each edited by the thin client terminals.

It is assumed that the thin client terminals 2a, 2b, and 2c are concurrently accessing and editing image data X included in same examination data. The original image data X and image data items X1, X2, and X3 each edited by the thin client terminals 2a, 2b, and 2c are shown in FIG. 9. Note that the image data X1 is updated data obtained by the thin client terminal 2a updating the image data X earlier than the other thin client terminals do, and both the image data X2 and the image data X3 are copied data. The image data items X1, X2, and X3 are collectively managed in an image data group Xx by the data managing unit 107 as data derived from the same image data X. The image data items X1, X2, and X3 each have different annotations (notes such as a comment and a sign). Specifically, the image data X1 has two circles, the image data X2 has a comment of "tumor" and an arrow, and the image data X3 has one circle.

Figure 10A:
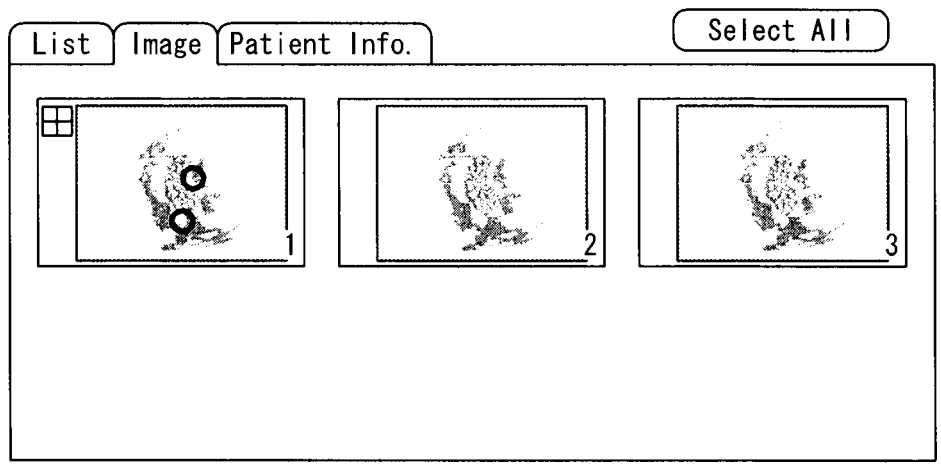
FIG. 10A is a diagram showing exemplary thumbnails of image data displayed on the thin client terminal if the copied data is generated.
Figure 10B:
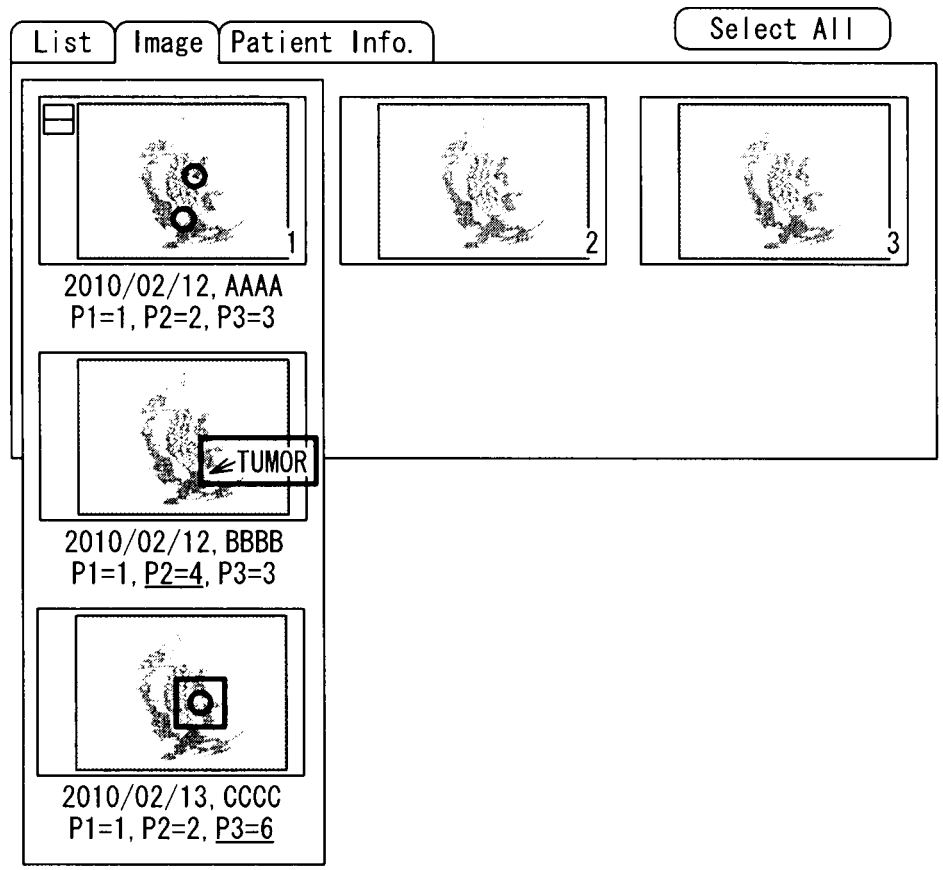
FIG. 10B is a diagram showing exemplary thumbnails of image data displayed on the thin client terminal if the item is expanded.
Figure 11:
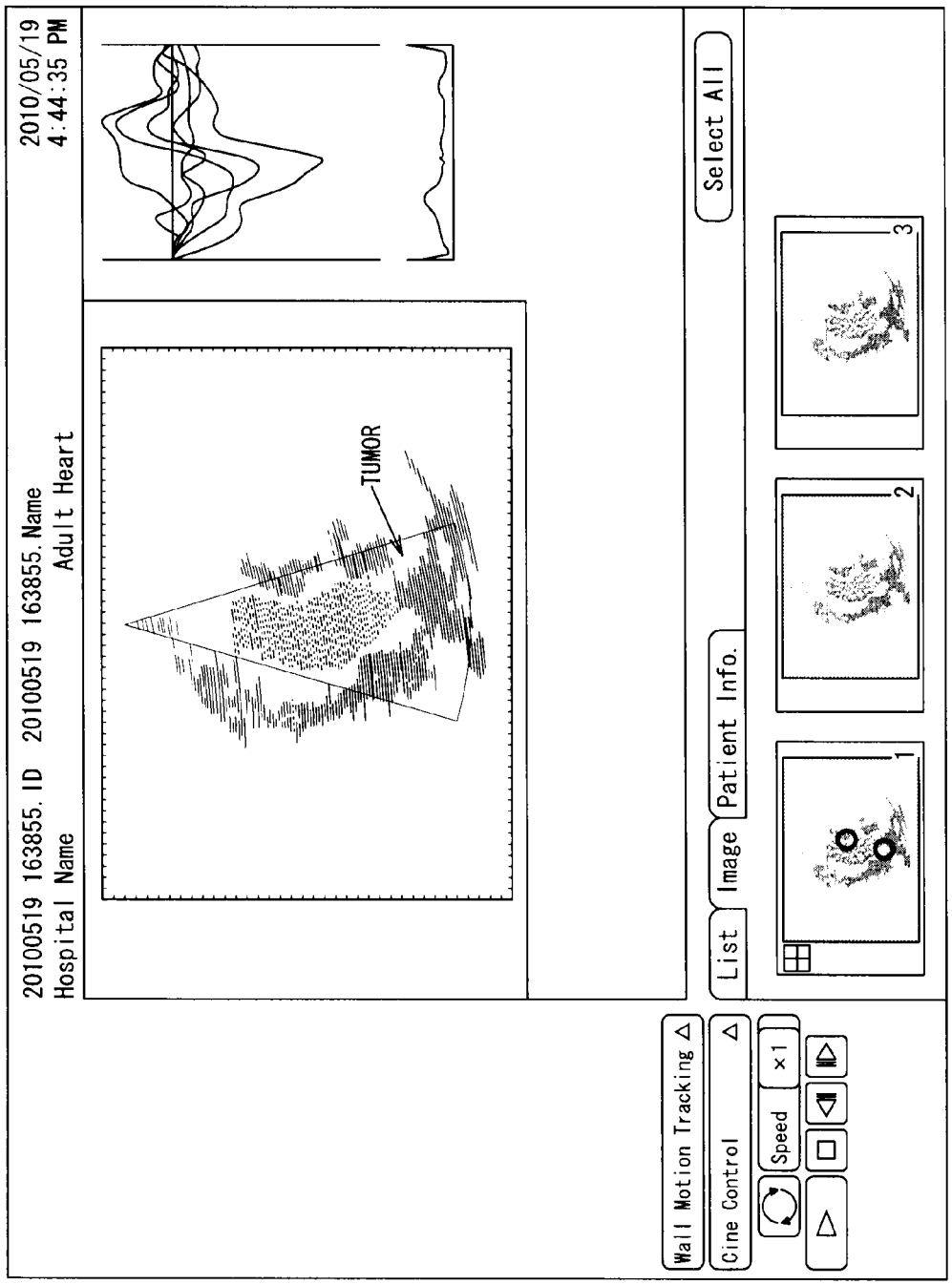
FIG. 11 is a diagram showing an exemplary display of details of the image data.

Exemplary thumbnails of image data displayed on the thin client terminal 2a are shown in FIG. 10A and FIG. 10B. Exemplary display of details of the image data is shown in FIG. 11. Because copied data (image data items X2 and X3) is attached to the image data X1, a + sign is added to a corner of a frame for the image data X1 (FIG. 10A). If this + sign is selected, thumbnails of all the copied data are expanded and simultaneously displayed (FIG. 10B). Under each thumbnail, for example, a data updated date, a person who updates the data, and set values of parameters are displayed. At this time, in the displayed image data items X2 and X3, a part different from the image data X1 (e.g., an annotation) may be highlighted by surrounding it with a frame, for example. If a set value of a displayed parameter is different from that of the image data X1, highlights such as bold or colored characters and an underline may be used.

If any one of the displayed thumbnails is further selected, as shown in FIG. 11, details of the image data corresponding to the selected thumbnail (image viewer) are displayed. For example, the image viewer displays enlarged image data as well as detailed set values of the display parameters.

<Image Data Output>

Next, an exemplary operation to output the above-described image data group Xx to an external storing device and medical equipment will be described with reference to FIG. 12. The data outputting unit 108 of the server 1 that receives from the thin client terminal 2a a request to output the image data group Xx outputs data included in the image data group Xx based on a predetermined condition. As with the case of FIG. 8, the output complies with the standard of the medical equipment, the DICOM format. Examples of the predetermined condition involving the output include the three ways shown in FIG. 12.

Figure 12:
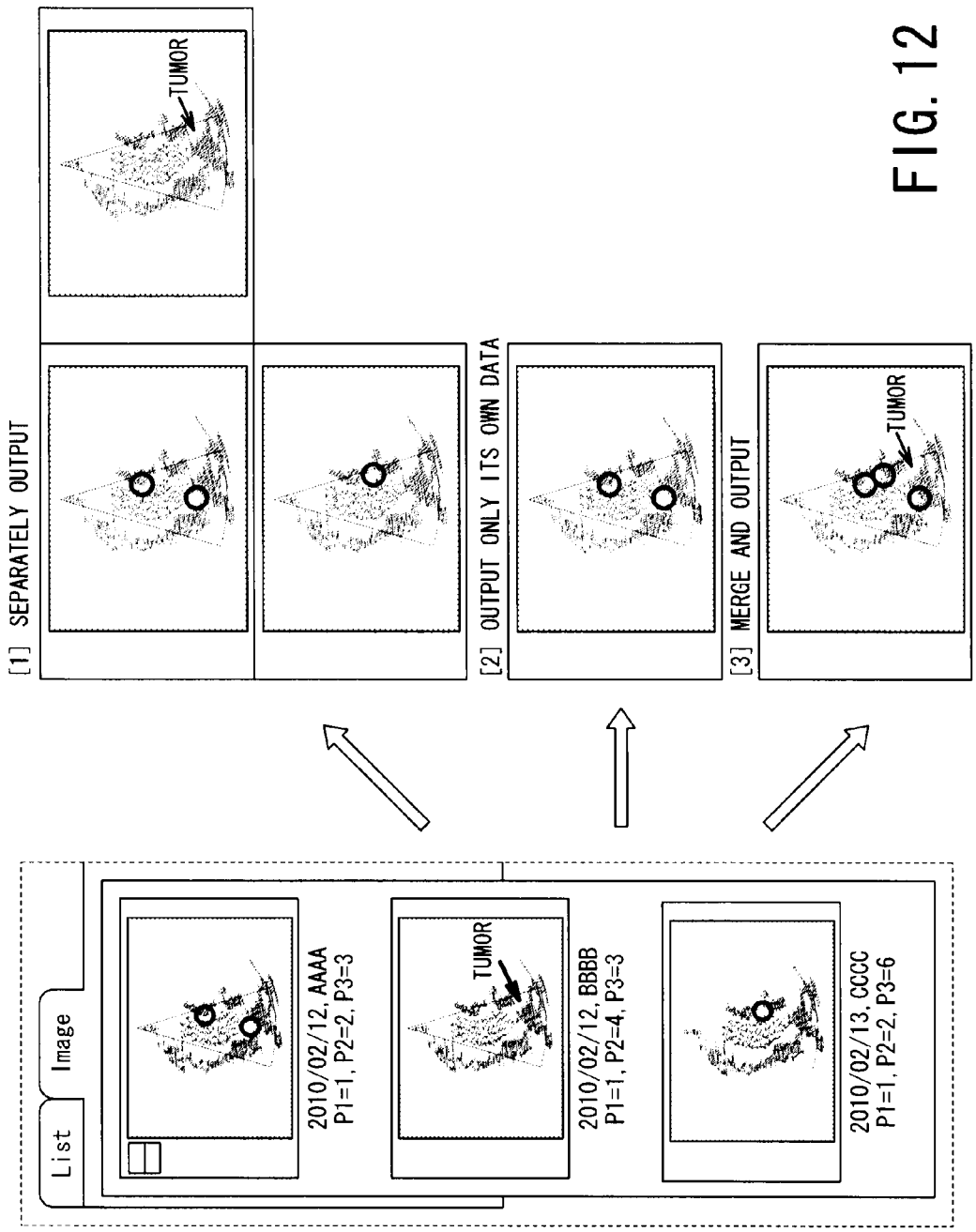
FIG. 12 is a conceptual diagram if image data group is output to the external storing device and the medical equipment.

In a first example shown in [1] of FIG. 12, the data outputting unit 108 of the server 1 separately outputs all the image data items X1, X2, and X3 included in the image data group Xx. However, as with the case of [1] in FIG. 8, when the data is output, information that each of the image data items X1, X2, and X3 is derived from the image data X (that is, information that the image data items X1, X2, and X3 are included in the image data group Xx) is added to "Private Data" of each of the image data items X1, X2, and X3. Thereby, when the data output to the external medical equipment is returned and stored into the server 1, because each of the image data items X1, X2, and X3 holds by "Private Data" the information that the data items are included in the image data group Xx, each of the image data items X1, X2, and X3 can be restored to the original state of data. As a result, the server 1 can display the data list on the thin client terminals 2 based on the image data items X1, X2, and X3 returned to the server 1 and the added information.

In a second example shown in [2] of FIG. 12, the server 1 outputs only the data edited by the thin client terminal that issues an output request. For example, if the thin client terminal 2*a* issues an output request to the server 1, the server 1 outputs only the image data X1.

In a third example shown in [3] of FIG. 12, the server 1 merges and then outputs the image data items X1, X2, and X3 in the image data group Xx. That is, modifications in the image data items X1, X2, and X3, for the original image data X are merged into one data set, the modification data set is made to the original image data, and then the resultant image data is output.

For example, if the image data items X1, X2, and X3 are merged and output, because the image data items each have different annotations on the original image data X, all the annotations are added to the original image data X and then the resultant image data is output. Specifically, all the annotations, namely, the two circles on the image data X1, the comment of "tumor" and the arrow on the image data X2, and the one circle on the image data X3 are added to the original image data X, and then the resultant image data is output.

It should be noted that a condition to output the image data in FIG. 12 may be changed according to an output destination. For example, if the image data is output to a medium such as a CD-ROM, only the data edited by the thin client terminal that has issued the output request may be output because of a limited data amount. If the image data is output to another server, all the image data items may be separately output.

<Report Renewal>

Also when the examination data includes text data such as a report, such text data can be treated in the same manner as image data. The case in which a plurality of thin client terminals are concurrently accessing a report will be described below.

Figure 13:
FIG. 13 is a diagram showing an original report included in same examination data, and reports each edited by the thin client terminals.

It is assumed that the thin client terminals 2*a* and 2*b* are concurrently accessing and editing a report Y included in same examination data. The original report Y as well as a report Y1 edited by the thin client terminal 2*a* and a report Y2 edited by the thin client terminal 2*b* are shown in FIG. 13. Note that the report Y1 is updated data obtained by the thin client terminal 2*a* updating the report Y earlier than the thin client terminal 2*b*, and the report Y2 is copied data. These reports Y1 and Y2 are collectively managed in a report group Yy by the data managing unit 107 as data derived from the same report Y. Each of the reports Y1 and Y2 has an additional description to the report Y.

Figure 14A:
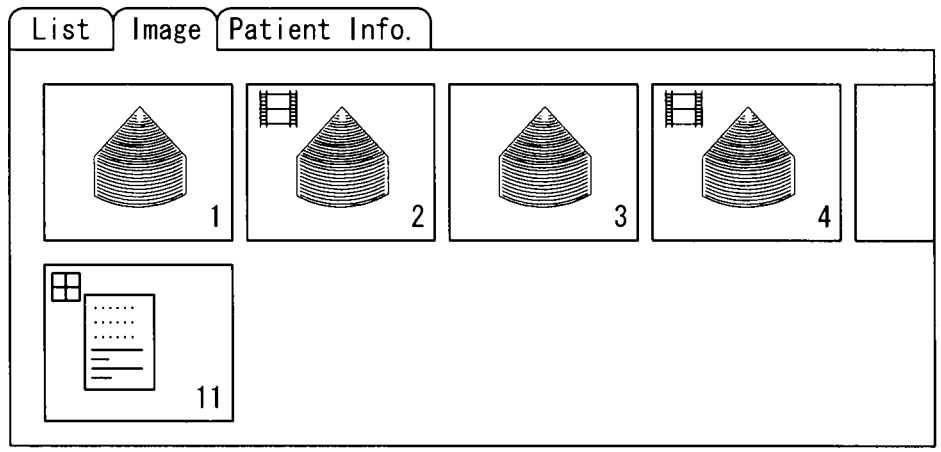
FIG. 14A is a diagram showing exemplary thumbnails of image data displayed on the thin client terminal if the copied data is generated.
Figure 14B:
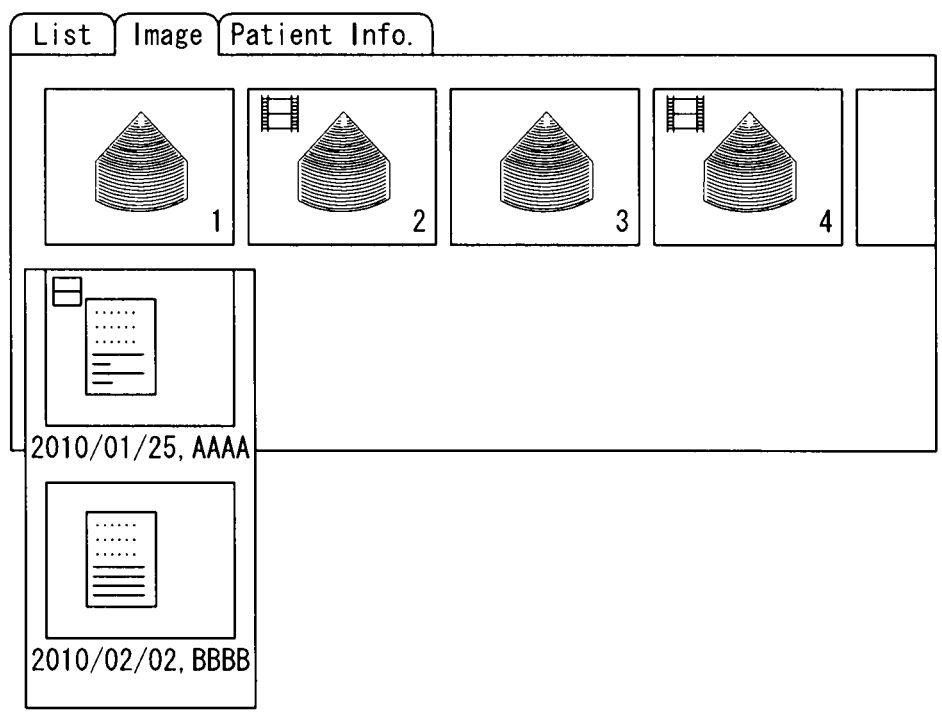
FIG. 14B is a diagram showing exemplary thumbnails of image data displayed on the thin client terminal if the item is expanded.

An example of thumbnails displayed on the thin client terminal 2*a* is shown in FIG. 14A and FIG. 14B. Exemplary display of details of the report is shown in FIG. 15. Because copied data is attached to the report Y1, a + sign is added to a corner of a frame for the report Y1 (FIG. 14A). If this + sign is selected, thumbnails of the copied data of all the reports are expanded and simultaneously displayed (FIG. 14B). Under each thumbnail, for example, a data updated date and a person who updates the data are displayed. At this time, in the displayed thumbnails of the reports Y1 and Y2, a part different from the original report Y may be highlighted by an underline, a bold, or the like. If any one of the displayed thumbnails of the reports is further selected, as shown in an example of FIG. 15, details of the reports in the selected thumbnail (report viewer) are displayed.

The editing described above may be made by editing data such as images at the thin client terminal as well as by editing data at the server in response to an operation through the thin client terminal.

According to the embodiments described above, in a thin-client-based network, if a thin client terminal requests to update data on a server and a last update time of the data is later than an access start time of the thin client terminal, the server decides that another thin client terminal is concurrently accessing the same data and has edited this data. The server then generates and stores copied data without updating the data. Therefore, with respect to data edited by any one of the thin client terminals edits data, the server determines whether to update original data or to generate copied data, so that even if a plurality of thin client terminals are concurrently accessing same data, the case in which only editing by a thin client terminal that has performed updating earlier can be made to the data does not occur. Furthermore, data updated by a thin client terminal can be prevented from being deleted accidentally by another thin client terminal.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing server connected with a plurality of terminals via a network, the server comprising:
a storing unit configured to store medical image data;
an access time obtaining unit configured to obtain an access start time at which each of the terminals accesses medical image data selected by each of the terminals;
an update time obtaining unit configured to, if each of the terminals edits the medical image data and issues an update request for an edited version, obtain a last update time of the edited version;
a determining unit configured to, if one of the terminals issues the update request, determine whether to update the medical image data with the edited version or copy the edited version, based on the access start time obtained by the terminal and the last update time obtained by another of the terminals, to thereby generate updated data being a substitute for an original of the medical image data or copied data independent of the original; and
a data outputting unit configured to output the updated data and the copied data as data derived from the medical image data.

2. The medical image processing server according to claim 1, wherein
the determining unit is configured to generate the edited version, for which the terminal issues the update request, as the updated data if the access start time obtained by the terminal is later than the last update time obtained by the other terminal, and
the determining unit is configured to generate the edited version, for which the terminal issues the update request, as the copied data if the access start time obtained by the terminal is earlier than the last update time obtained by the other terminal.

3. The medical image processing server according to claim 2, further comprising:

a display controlling unit configured to allow each of the terminals to display a list of the derived data.

4. The medical image processing server according to claim 3, wherein the data outputting unit is configured to output all the derived data items generated in response to the update requests from the terminals.

5. The medical image processing server according to claim 3, wherein the data outputting unit is configured to output, of all the derived data items generated in response to the update requests from the terminals, only derived data generated in response to an update request from a specific terminal.

6. The medical image processing server according to claim 3, wherein the data outputting unit is configured to, if a plurality of data items derived from a single medical image data item are generated in response to the update requests from specific terminals of the terminals, merge a modified portion that is in each of the derived data items into each of the derived data items and output the result.

7. The medical image processing server according to claim 6, wherein the medical image data is diagnostic image data obtained by a diagnostic imaging equipment.

8. The medical image processing server according to claim 3, wherein different annotations are attached to the derived data items.

9. The medical image processing server according to claim 2, further comprising:

a display controlling unit configured to obtain the derived data output by the data outputting unit and identification information of the derived data and to, based on the obtained derived data and the identification information of the obtained derived data, cause each of the terminals to display a list of the derived data items.

10. A managing method for a medical image processing server connected with a plurality of terminals via a network, the method comprising:

obtaining an access start time at which each of the terminals accesses medical image data selected by each of the terminals;

obtaining, if each of the terminals edits the medical image data and issues an update request for an edited version, a last update time of the edited version;

determining, if one of the terminals issues the update request, whether to update the medical image data with the edited version or copy the edited version, based on the access start time obtained by the terminal and the last update time obtained by another of the terminals, to thereby generate updated data being a substitute for an original of the medical image data or copied data independent of the original; and outputting the updated data and the copied data as data derived from the medical image data.

\* \* \* \* \*